United States Patent [19]
Larsen et al.

[11] Patent Number: 5,242,891
[45] Date of Patent: Sep. 7, 1993

[54] METHODS FOR FRUIT THINNING COMPRISING APPLYING FATTY ACIDS OR DERIVATIVES THEREOF TO FLOWERS

[75] Inventors: Thomas E. Larsen, Oceanside; Kenneth D. Abercrombie, Sanger; R. Hugh Crowley, Oceanside, all of Calif.

[73] Assignee: Mycogen Corporation, San Diego, Calif.

[21] Appl. No.: 877,009

[22] Filed: May 1, 1992

[51] Int. Cl.$^5$ .................. A01N 37/00; A01N 43/20; A01N 53/00; A01N 57/04
[52] U.S. Cl. .................. 504/127; 504/140; 504/142; 504/166; 504/171
[58] Field of Search ............ 71/106, 113; 504/166, 504/171, 127, 142, 149, 140

[56] References Cited

U.S. PATENT DOCUMENTS 2,626,862 6/1950 Zimmerman et al. ............... 71/2.7
4,975,110 12/1990 Puritch et al. ...................... 71/113
5,035,741 7/1991 Puritch et al. ...................... 71/113

FOREIGN PATENT DOCUMENTS 0463241 6/1990 European Pat. Off. .

OTHER PUBLICATIONS

Tso, T. C., G. L. Steffens and M. E. Engelhaupt (1965), "Inhibition of Tobacco Auxiliary Bud Growth with Fatty Acid Methyl Esters", *J. Agr. Food Chem.* 13(1):78-81.

Sill, Lois Z., and Paul V. Nelson (1970), "Relationship Between Azalea Bud Morphology and Effectiveness of Methyl Decanoate, A Chemical Pinching Agent", *J. Amer. Soc. Hort. Sci.* 95(3):270-273.

Chase, A. R. and L. S. Osborne (1983), "Influence of an Insecticidal Soap on Several Foliar Diseases of Foilage Plants", *Plant Disease* 67(9):1021-1023.

Ahmed, S. M., Fasih Ahmad and S. M. Osman (1985), "Preparation and Characterization of Derivatives of Isoricinoleic Acid and Their Antimicrobial Activity", *JAOCS* 62(11):1578-1580.

Yoshikua, Frank T. and R. Scott Johnson (1989) Chapter 10 In: LaRue, J. H., R. S. Johnson, eds. *Peaches Plums, and Nectarines—Growing and Handling for Fresh Market*, University of Calif. Coop. Ext. Serv. Publication #3331.

Skoog, F. *Plant Growth Substances* 1979. NY:Springer-Verlag p. 411, 1980.

*Primary Examiner*—Richard L. Raymond
*Assistant Examiner*—S. Mark Clardy
*Attorney, Agent, or Firm*—Saliwanchik & Saliwanchik

[57] ABSTRACT

The invention described here concerns the unique utility of fatty acids and their derivatives to act as fruit thinning agents. Proper use of the methods and compositions will result in the advantageous thinning of fruit which can improve the quality of the harvested fruit and result in more consistent crops from one year to the next.

16 Claims, 6 Drawing Sheets

METHODS FOR FRUIT THINNING COMPRISING APPLYING FATTY ACIDS OR DERIVATIVES THEREOF TO FLOWERS

BACKGROUND OF THE INVENTION

The practice of fruit thinning is a standard management procedure for the deciduous fruit industry. Thinning is the removal, or prevention, of a part of the fruit crop before it matures on the tree. The fruit itself may be targeted, or the blossoms which produce the fruit may be the target of the thinning procedure. Fruit thinning is necessary since many fruit trees tend to produce far too many blossoms each year. The excess of fruit blossoms and fruit often results in produce which is too small to be marketable. Further, when the fruit density is too great on portions of the fruit trees, the weight of the fruit may become too large to be supported by the tree, and the entire branch, including its fruit, may be lost. Additionally, fruiting is an exhaustive process to the tree, especially if the crop is heavy. Therefore, one advantage to fruit thinning is to permit the tree to mature as large a crop as possible and yet converse sufficient nutrients and carbohydrates for good shoot and spur growth, leaf development, and flower-bud formation for next year's crop. If the tree is permitted to mature an excessive crop, it becomes devitalized to the point where it not only produces an inferior product, but it becomes increasingly susceptible to disease and low-temperature injury.

An additional problem pertains to certain types of fruit trees which have substantially reduced fruit yields in alternate years. These biennial fruits have excessively large crops followed by insufficient crops in alternate years. This pattern can be disrupted, and constant desirably-sized crops can be obtained on a regular basis by proper thinning techniques. Apples are a very good example of biennial fruits which respond favorably to appropriate thinning.

There are three commonly-used methods for thinning fruit: mechanical, chemical, and by hand. Each has its advantages and disadvantages. In practice, fruit thinning is generally done by hand. Workers must go to each tree and remove sufficient fruit to provide satisfactory fruit thinning. Hand labor is perhaps the most reliable, but it is expensive.

Chemical thinning would be preferred from a cost standpoint, but environmental concerns, as well as inconsistent results, are major drawbacks to existing chemical methods. The inconsistent results include overthinning, underthinning, and foliage injury. The chemical thinning procedures which have been used in the past, and which are currently in use, function through a variety of mechanisms. Some chemicals are applied during bloom and work by burning the pistil to prevent pollination. Other chemicals are applied during various stages of early fruit development to induce fruit drop (Yoskikua and Johnson [1989] Chapter 10 In: LaRue, J. H., R. S. Johnson, eds. Peaches, Plums, and Nectarines-Growing and Handling for Fresh Market, University of California Coop. Ext. Serv. Publication #3331). The success of chemical fruit thinning strategies can depend upon a number of factors including: variety and strain, tree condition, fruit set, proximity to pollinizers, weather, the chemical used, and the specific application protocol.

Among the early chemicals which were used for fruit thinning were tar-oil distillates such as phenols. These compounds were typically sprayed on the trees a day or two prior to full bloom. In the 1960s, several postbloom thinners were introduced, including methyl carbamates (Sevin 50% from Rhone-Poulenc). One method of chemical thinning uses growth regulators to reduce the amount of fruit and to overcome alternate year or biennial bearing. Certain alkoxylated amines have been described as useful for thinning stone fruit blossoms. See, for example, EPO 463 241. Some growers may use several different chemicals, or combinations of chemicals, during the bloom and postbloom period.

Several chemicals have been or are currently being used in the industry for fruit thinning purposes. Some of these existing products are toxic to both the surrounding environment as well as the operators that are charged with the task of applying these chemical agents. Furthermore, many of the existing products are also phytotoxic to the orchard.

One chemical thinning agent is DNBP (Gebutox TM 50% from Hoechst). This agent effectively reduces the number of blossoms on stone fruit trees and leads to increased fruit size. However, the agent has been found to be phytotoxic to the fruit trees and other plants as well. Further, the application of this agent poses some risk to the person applying it. DNOC (Elgetol TM from FMC) was a major product used for apple thinning. However, this product has been removed from the market because of toxic properties.

Another agent which has been used for fruit thinning is Paraquat. However, this agent has been found to be toxic to humans and to cause damage to the crop treated as well as other surrounding plants. Both DNBP and Paraquat are now withdrawn from governmental approval in many countries for use in blossom thinning of stone fruit for reasons of toxicological concern and orchard safety.

Currently, the only thinning agents available to growers are NAA (Fruitone®N from Rhone-Poulenc), ethephon, and NAD (Amid-Thin®W from Rhone-Poulenc). These agents are growth regulator type materials and provide inconsistent results. Growers can also use the insecticide Sevin, but this material kills the bee population needed for pollination. Accordingly, there exists a need in the fruit industry for a chemical blossom thinning agent which exhibits a relatively low phytotoxicity, is not harmful to humans applying the agent, does not damage pollinator populations, and is capable of providing acceptable and consistent results in blossom thinning and the subsequently required fruit thinning effect. These and other objects of the present invention will be apparent from the summary and detailed description that follow.

Fatty acids are a class of natural compounds which occur abundantly in nature and which have interesting and valuable biological activities. The in vitro activity of fatty acids against many medically important fungi and bacteria is well known. Ahmed et al. ([1985] JAOCS 62:1578-1580) report in vitro inhibition of radial growth of several fungal genera with plant pathogenic representatives. Recently there has been an expanding use of "insecticidal soaps" in agriculture which are salts of certain fatty acids. This has resulted in a few observations of impact on fungal disease. For instance, Chase et al. ([1989] Plant Disease 67:1021-1023) observed that applications of a c18:1 fatty acid salt "insecticidal soap" gave moderate preventive control of two foliage plant diseases and actually exacerbated two other diseases.

Recently, salts of fatty acids, primarily sodium or potassium fatty acid salts, have been used commercially as insecticides. Compositions having excellent insecticidal properties which exploit these salts are available commercially from Mycogen Corporation, under the trademark M-PEDE. A herbicidally active composition utilizing partially saponified fatty acids as the active ingredient is sold by Mycogen under the trademark SHARPSHOOTER. These fatty acid compositions are effective, naturally-occurring pesticides which have no known long-term environmental effects.

U.S. Pat. Nos. 2,626,862; 4,975,110; and 5,035,741 describe certain fatty acid compositions useful as herbicides. These patents also teach that the proper formulation of a fatty acid herbicide requires one or more surfactants. Also, fatty acid esters have been used as chemical pinching agents for the inhibition of bud growth of certain plants (Tso, T. C., G. L. Steffens, M. E. Engelhaupt [1965] J. Agr. Food Chem. 13(1):78-81; Sill, L. Z., P. V. Nelson [1970] J. Amer. Soc. Hort. Sci. 95(3):270-273). There are no reports in the literature on the use of fatty acids or their salts, esters, or other derivatives as fruit thinning agents.

BRIEF SUMMARY OF THE INVENTION

The subject invention pertains to the discovery that fatty acids and their derivatives, when used at the appropriate concentration range and timing, are useful for fruit thinning. Thus, the subject invention provides parameters of application which allow the useful application of these agents for the thinning of fruit.

Specifically, fruit can be effectively thinned by appropriate application of compositions comprising one or more substituted (or unsubstituted) saturated (or unsaturated) fatty acids (or their salts or esters). The fatty acids of the subject invention can be from about C7 to about C20 and can be, for example, in the epoxide, lactone, cyclopropane, methylated, or hydroxylated forms. The fatty acids of the subject invention can be represented by the following formula:

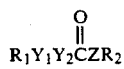

wherein
Z = O, N, or S
$R_1$ = C5 to C19 saturated or unsaturated hydrocarbon, or an epoxide, or cyclopropane thereof
$Y_1$ = H, $C_1$-$C_5$ hydrocarbon, or hydroxyl at any position along $R_1$
$Y_2$ = H, $C_1$-$C_5$ hydrocarbon, or hydroxyl at any position along $R_1$
$R_2$ = $C_1$-$C_{10}$ saturated or unsaturated, branched or unbranched, hydrocarbon which may have one or more hydroxyl groups at any position on $R_2$; carbohydrate; salt; or H.

In a preferred embodiment of the invention, $R_2$ is selected from the group consisting of aliphatic amines which form cationic aliphatic ammonium compounds; K+; Na+; and H+. Oleic, linoleic, linolenic, and pelargonic acids and their salts and esters are particularly useful according to the subject invention. We have found that the monoethylene glycol ester of fatty acids is particularly useful according to the subject invention. In addition to the groups specified above, $R_2$ may be selected from a variety of groups which would be readily evident to a person skilled in this art using the teachings of the subject invention.

Specifically exemplified herein are saturated and mono-unsaturated fatty acids. The use of the compositions described here, when used in the proportions and application rates set forth more fully hereinafter, results in an advantageous thinning of fruit. This activity is most advantageous over a range of concentrations between low doses which are ineffective and higher doses which are phytotoxic to the fruit tree. This critical range varies with the form of the fatty acid (free acid, salt, ester, or formulation type) and the fruit under consideration, but can be determined by a person skilled in this art using the teachings of the subject invention.

The compounds used according to the subject invention are exemplified by C9 (pelargonic) fatty acid and its salts and esters. These compounds, which exhibit fruit thinning activity, can be combined with other such thinning agents. These other fruit thinning agents may be, for example, chemical agents. The specific combination of ingredients can be manipulated to provide the optimal composition for a particular application. It is within the skill of a person trained in this art to use the teachings presented herein to prepare appropriate compositions for use in a specific application.

The fatty acids of the subject invention and their derivatives are highly advantageous for fruit-thinning use because they occur commonly in nature, have little mammalian toxicity, are compatible with other thinning strategies and are readily broken down to innocuous components.

Thus, a primary advantage of the subject invention is that it provides a safe, effective chemical thinning agent which reduces the number of viable blossoms on a fruit tree during the blossom period to thereby provide a tree having a lower fruit density thereon. In this manner, overloading of sections of the tree can be avoided and larger fruit can be produced since the same amount of sustenance will be supplied to a smaller number of viable fruit. Furthermore, constant crop volumes for normally biennial fruit can be achieved.

DETAILED DESCRIPTION OF THE INVENTION

Figure 1:
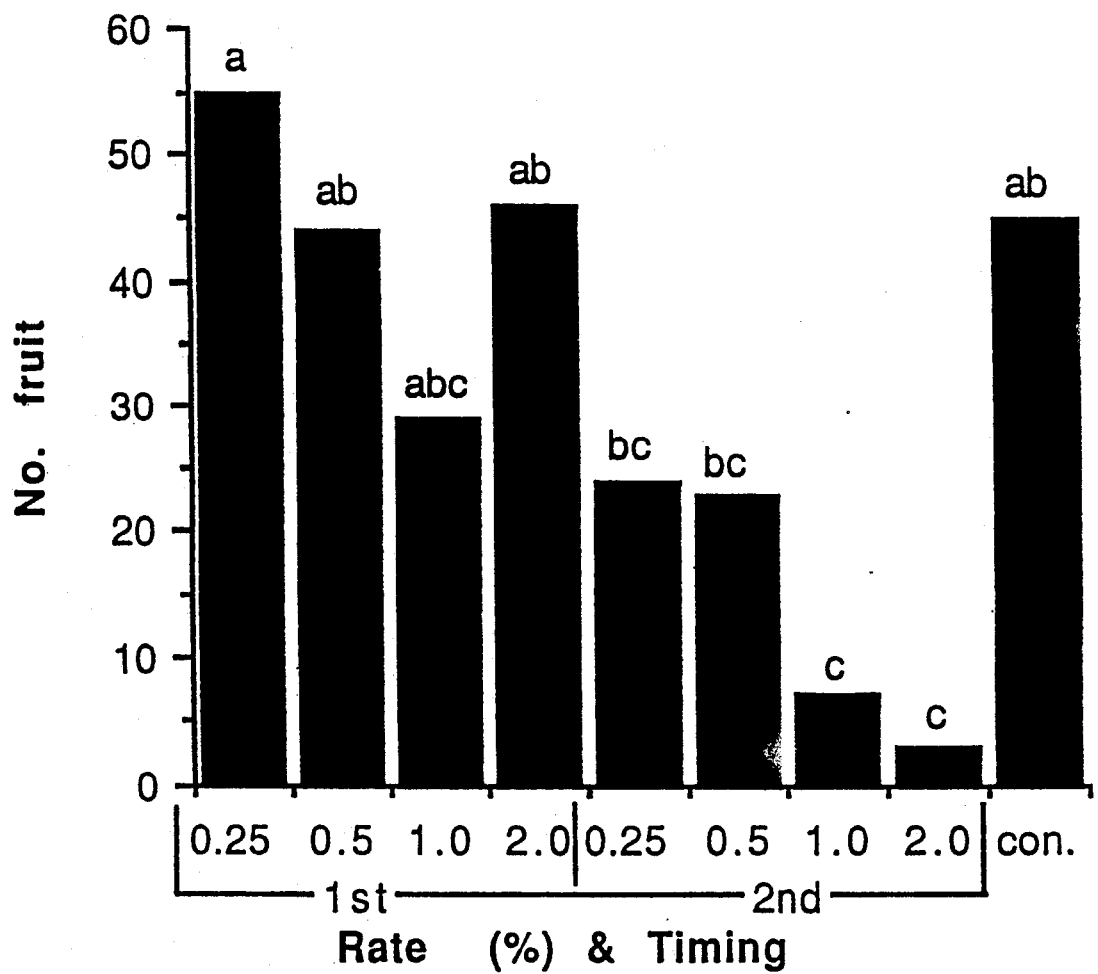
FIG. 1 shows mean numbers of fruit per limb ten weeks after treatment and at harvest.

The subject invention concerns the use of fatty acids and their derivatives for fruit thinning. The fatty acids used according to the subject invention can be unsubstituted, or substituted, saturated, or unsaturated, fatty acids (or their salts or esters), of about C7 to about C20. Specifically exemplified are fatty acids of length C9 typified by, but not limited to, pelargonic acid and various salts and esters of this acid. The fatty acid component of the subject invention may be a single fatty acid, ester, or salt, or a mixture of two or more such compounds.

One embodiment of the present invention consists of the application of a fatty acid compound. A further embodiment contemplates application of a fatty acid with another thinning agent. The combination of agents may be applied sequentially or as a tank mix. Tank mixes of fatty acids with other thinning agents can be prepared according to procedures which are well known to those skilled in the art.

A fatty acid spray can be prepared using a solvent solution or emulsion of the fatty acid, a surfactant, and sufficient water to dilute the mixture to the desired concentration. Salts of fatty acids are readily dispersable or soluble in water. Salts which can be used according to the subject invention are well known to those skilled in the art. For example, sodium and potassium salts can be readily prepared and used according to the subject invention. Amine salts can also be used according to the subject invention. With reference to the chemical formula presented in the Brief Summary of the Invention, the amine salts which are useful in the subject invention may be identified as having $R_2$=a salt-forming moiety chosen from the group consisting of aliphatic amines which form cationic aliphatic ammonium compounds.

The surfactants which may be used to emulsify the fatty acid in the aqueous formulations can be any of the non-phytotoxic surfactants, which are customarily used in preparing formulations for use on agricultural crops. The composition of the subject invention may also be combined with a spray oil as described in U.S. Pat. No. 4,560,677.

One element of this invention concerns the range for the efficacious use of fatty acids. At very low concentrations there is little to no thinning activity, at an intermediate range there is desirable activity, but at higher concentrations the foliage of the plant can be damaged and this can result in disease, infection, or other detrimental effects. Appropriate formulations and concentrations can be readily ascertained by those skilled in this art using the teachings of the subject invention.

The methods and compositions of the subject invention are useful for thinning fruit on a variety of different fruit-bearing plants. Specifically, the subject invention can be used for thinning pome fruits and stone fruits. These categories are well known to those skilled in the art. For example, apples and pears are typical pome fruits while peaches and plums are typical stone fruits. The subject invention could be practiced on other members of the pome and stone fruit categories. Also, a person skilled in this art, and utilizing the teachings of the subject invention, could thin other categories of fruit as well.

As described in the examples which follow, the application of a fatty acid composition, according to the subject invention, should take place while the fruit tree is in bloom. The person skilled in this art, using the teachings of the subject invention, can determine the optical timing and concentration of the application. The application can be made, for example, during the time period from about 10% bloom to about 3 to 5 days after 100% bloom. One hundred percent bloom is defined as the time when all of the blossoms have just opened. Preferably, application will take place after 60% bloom and, most preferably, as the bloom reaches about 100%. For example, the application of the fatty acid composition may be done during the period from about 2 days before 100% bloom to about 2 days after 100% bloom.

The compositions are applied at concentrations ranging from about 0.05% to about 5.0% active ingredient (a.i.) by volume. To avoid problems of phytotoxicity and overthinning, concentrations of less than about 3.0% a.i. by volume are preferred.

The thinning composition is preferably applied in a manner similar to the manner in which commercially employed insecticides are used. More particularly, conventional equipment such as knapsack sprayers, hand held spray guns, mist blowers, and aerial spraying equipment among others may be used. The composition can be applied the same way as in normal pesticide application.

The process of the present invention has the significant advantages that it thins blossoms to the extent that hand thinning can be eliminated or considerably reduced. It can be done in a manner which is safe for the corps. The treatment has no long-term phytotoxic effect on the orchards if carried out correctly. The compounds are environmentally acceptable, present a low hazard to operators of the application equipment, and are non-corrosive to the equipment.

Following are examples which illustrate procedures, including the best mode, for practicing the invention. These examples should not be construed as limiting. All percentages are by volume of a 60% a.i. formulation, and all solvent mixture proportions are by volume unless otherwise noted.

EXAMPLE 1

Mycogen MYX-8714 was spray applied to 9-year old 'Rogers McIntosh'/M26 apple trees during blossoming. Mycogen MYX-8714 is an emulsifiable concentrate containing 60% by weight pelargonic acid prepared in an emulsion system of 9% by weight of emulsifier "RENNEX-31" (ICI), with the balance being ethylene glycol. Three replicate limbs per treatment were sprayed using a $CO_2$ pressurized backpack sprayer (30 psi) at 20-25% bloom and one day later at 60-70% bloom. Sufficient spray was applied to result in leaf and flower wetting without runoff. Treatments included MYX-8714 in water at 0.25, 0.5, 1.0, and 2.0% concentration (v/v) for each date with a single control (water only) applied at 20-25% bloom and 60-70% bloom. No surfactant was added to spray treatments. Blossom clusters per limb were counted three days prior to 20-25% bloom. Basal limb diameter was measured on the same date for calculation of limb cross-sectional area. The number of fruit remaining after treatment was counted ten weeks after treatment and again at harvest four months after treatment. Fruit weight, diameter, percent soluble solids, and firmness were obtained subsequent to harvest. A completely randomized design was used with statistical analysis (ANOVA) and mean separation by Duncan's Multiple Range.

Statistical analyses verified no significant differences in limb diameter, number of flower clusters or number of flower clusters per limb cross-sectional area, indicating an unbiased randomized design.

As shown in FIG. 1, the mean numbers of fruit per limb at ten weeks after treatment was related to rate and timing of treatment. Except for a high number of fruit remaining on limbs treated with the 2% spray at 20% bloom, the degree of thinning response was largely related to increasing concentration of MYX-8714. High fruit numbers in this treatment are in part explained by unusually high numbers of blossom clusters (>290) per limb on two of the three replicate limbs. Greatest fruit thinning occurred at 60% bloom indicating the thinning effect occurred largely on open blossoms.

Figure 2:
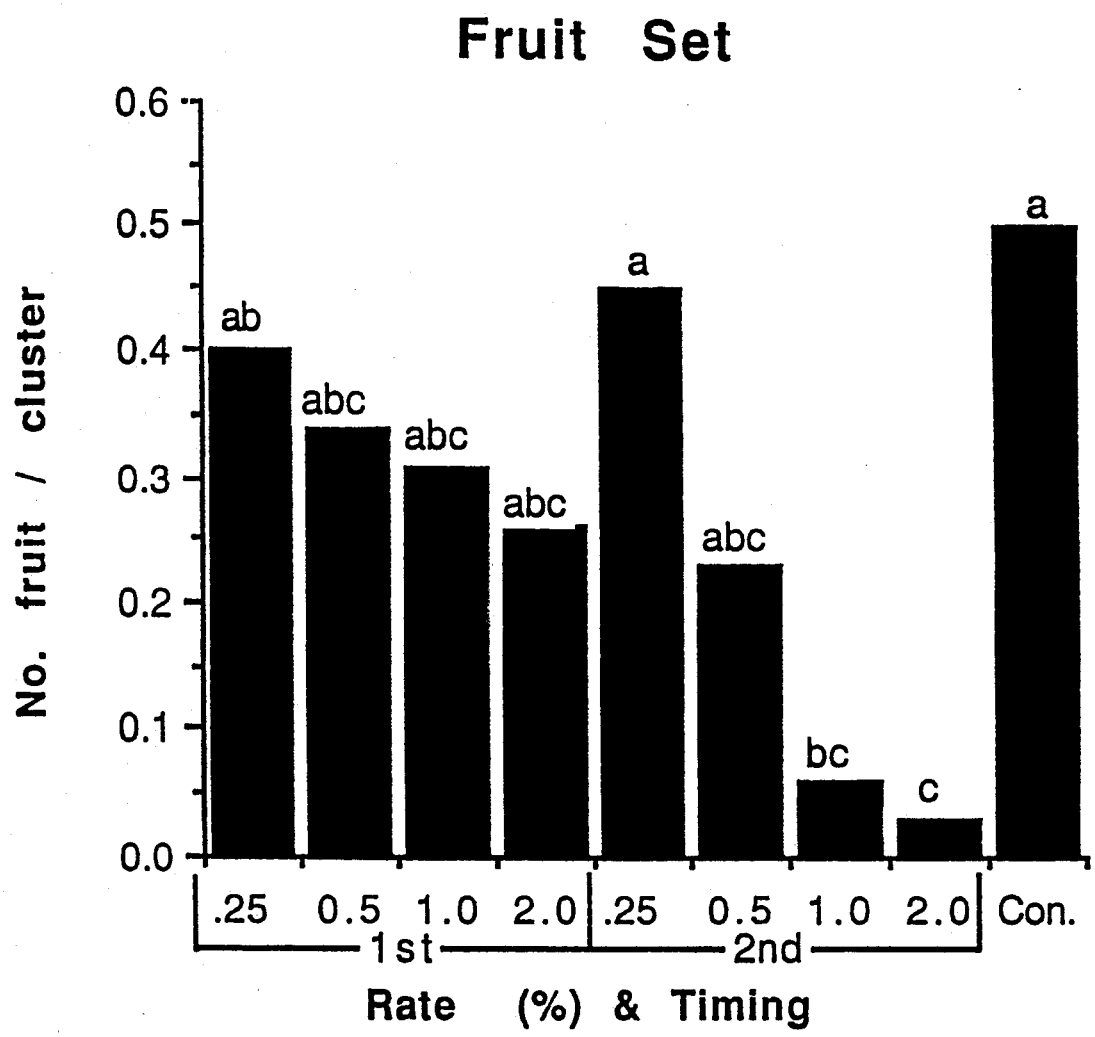
FIG. 2 shows the number of fruit per flower cluster.

As can be seen in FIG. 2, the fruit set (number of fruit per flower cluster) was low for all treatments including the control. The degree of blossom thinning was directly related to concentration of MYX-8714 and the percent open blossoms at the time of application. Excessive thinning occurred at high concentrations of the chemical applied at 60% bloom. The dosage-related thinning response suggest the degree of thinning is controllable, and the extent of thinning at any concentration can also be modified by the timing of the application.

Figure 3:
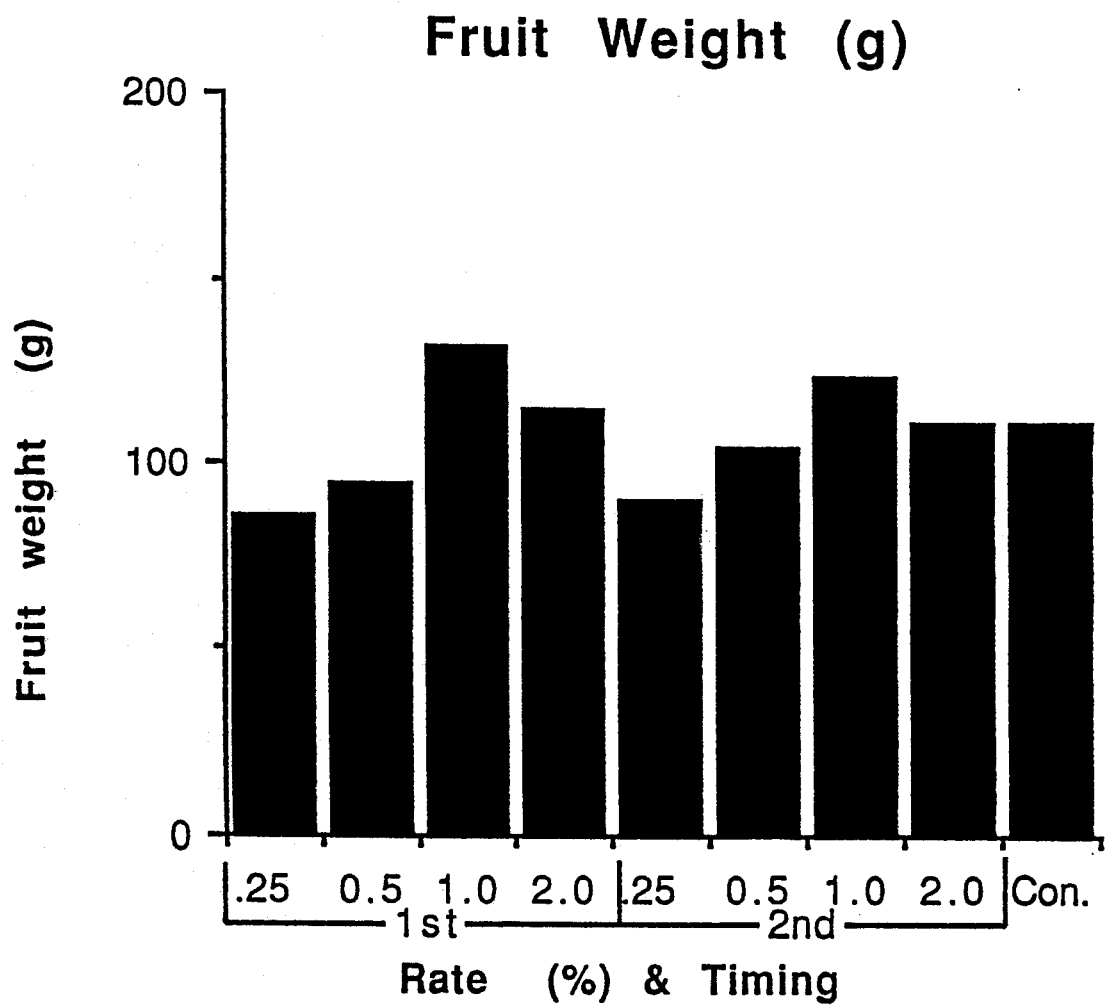
FIG. 3 shows mean fruit weight.

As shown in FIG. 3, mean fruit weight did not differ among treatments despite substantial reductions in fruit set at high concentrations of MYX-8714.

Figure 4:
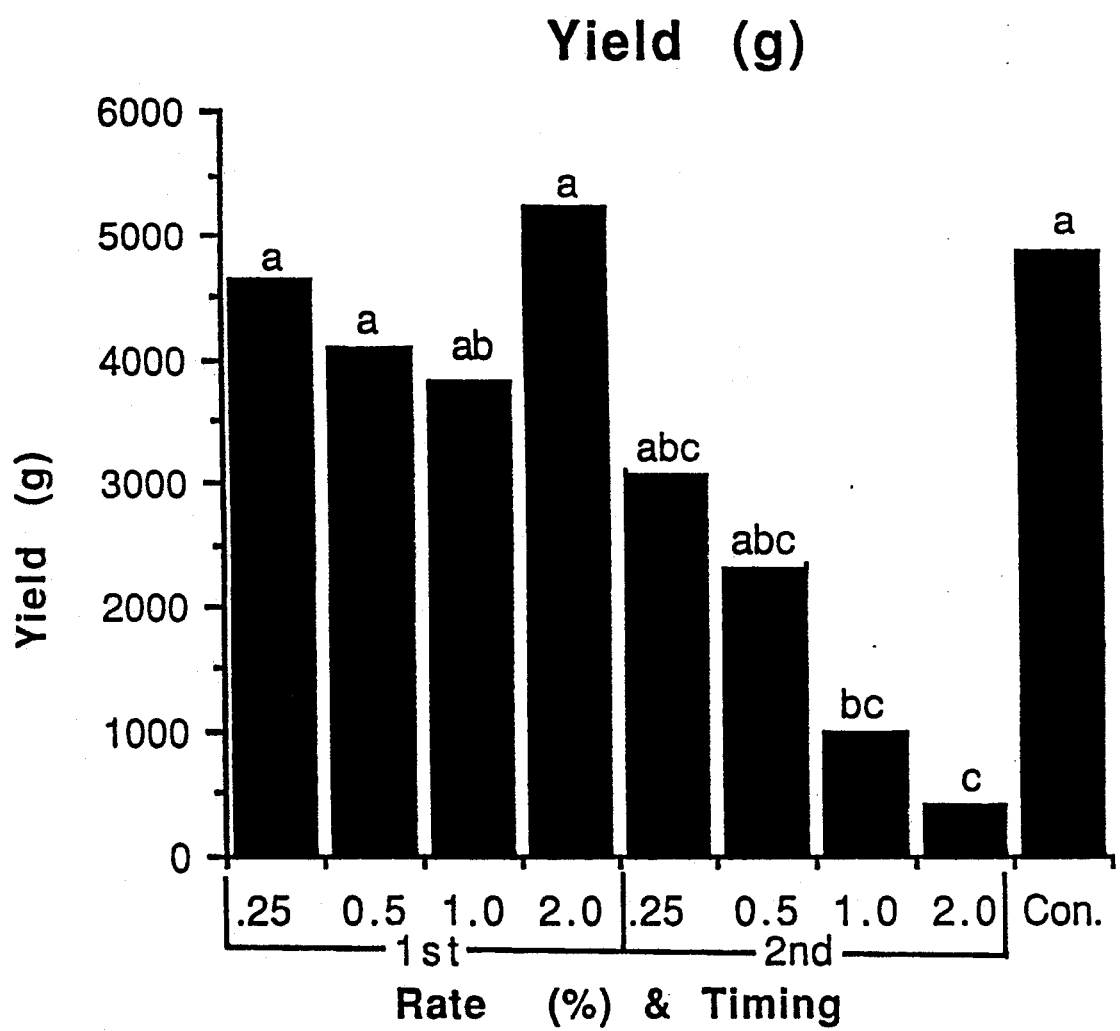
FIG. 4 shows fruit yield at harvest.

From FIG. 4 it can be seen that total fruit weight per limb paralleled the number of fruit at harvest since mean fruit weight was not affected by treatment. Reductions in yield on limbs thinned at 60% blossoming suggests that earlier or later applications during the blossoming period might be more effective in achieving optimum thinning.

Figure 5:
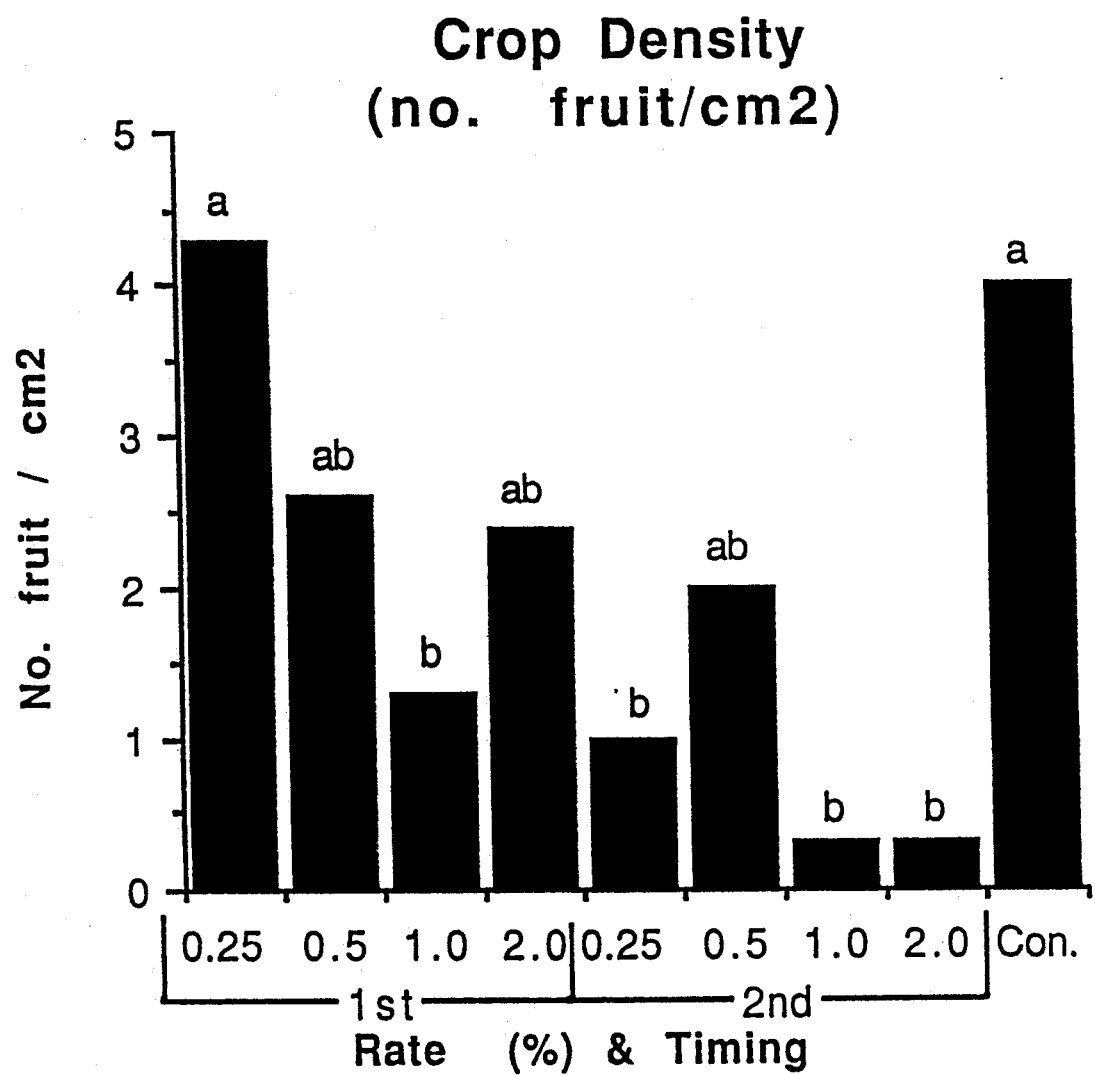
FIG. 5 shows crop density (fruit per cm$^2$ limb area) at different concentrations of MYX-8714.
Figure 6:
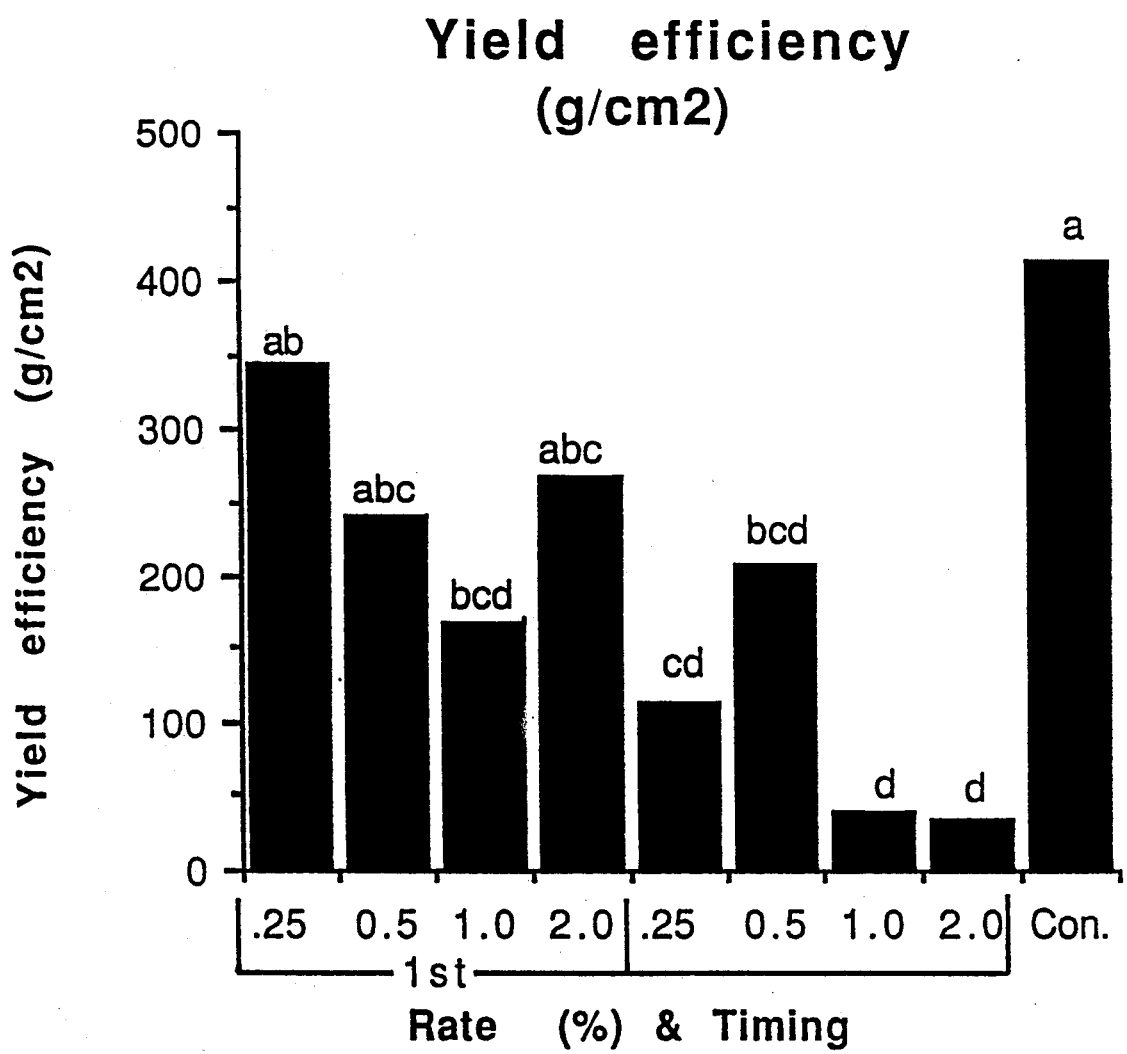
FIG. 6 shows yield efficiency (fruit weight per unit of limb area).

The number of fruit per cm² limb area indicates that the 0.25% concentration of MYX-8714 is optimum for thinning (FIG. 5). As shown in FIG. 6, fruit weight per unit of limb area (a measure of yield efficiency) paralleled fruit numbers. A trend to lower tree efficiency at the low concentration applied at 20% bloom suggests king or primary fruit may have been thinned, leaving smaller secondary fruit with less potential for increased size. A similar effect may have occurred at higher concentrations, where a trend to only slight compensation in greater yield was noted with reduced fruit numbers in treatments applied at 20% bloom.

No differences in fruit diameter, percent soluble solids, or fruit firmness due to treatment were measured at harvest. Thus, the dosage related response to MYX-8714 offers a significant benefit to fruit producers as a fruit thinner. More precise control of the degree of thinning than is possible with current fruit thinning programs is possible. Applications at early blossoming have the undesirable potential for preventing primary fruit set while allowing retention of late bloom and smaller fruit. Lower concentrations of the chemical applied later in the blossoming period can also reduce leaf injury, allowing for increased photosynthate during the critical postbloom fruit cell division period.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for thinning fruit, said method comprising the application of a fruit-thinning amount of a fatty acid, its salt, ester, or derivative, or mixture thereof, to the flowers of a plant.

2. The method, according to claim 1, wherein said fatty acid has the following formula:

$$R_1Y_1Y_2\overset{\overset{O}{\|}}{C}ZR_2$$

wherein
Z = O,
$R_1$ = C5 to C19 saturated or unsaturated hydrocarbon, or an epoxide, or cyclopropane thereof
$Y_1$ = H, $C_1$-$C_5$ hydrocarbon, or hydroxyl at any position along $R_1$
$Y_2$ = H, $C_1$-$C_5$ hydrocarbon, or hydroxyl at any position along $R_1$
$R_2$ = $C_1$-$C_{10}$ saturated or unsaturated, branched or unbranched, hydrocarbon which may have one or more hydroxyl groups at any position on $R_2$; carbohydrate; salt-forming cation or H.

3. The method, according to claim 2, wherein Z = O, and $R_2$ is selected from the group consisting of: aliphatic amines which form cationic aliphatic ammonium compounds; K; Na; and H.

4. The method, according to claim 3, wherein $R_2$ is isopropyl amine.

5. The method, according to claim 3, wherein said compound is a mono-glycol ester.

6. The method, according to claim 3, wherein said fatty acid is selected from the group consisting of caprylic acid, capric acid, undecylic acid, oleic acid, linoleic acid, linolenic acid, pelargonic acid, their salts and esters.

7. The method, according to claim 3, which comprises the application of two or more fatty acids, their salts or derivatives, sequentially or simultaneously.

8. The method, according to claim 1, wherein said fatty acid, its salt, ester, or derivative, is applied as a tank mix.

9. The method, according to claim 1, wherein said fatty acid, its salt, ester, or derivative, is applied either simultaneously or sequentially with another thinning agent.

10. The method, according to claim 9, wherein said thinning agent is selected from the group consisting of NAA, NAD, and ethephon.

11. The method, according to claim 1, wherein said fruit is selected from the group consisting of pome fruit and stone fruit.

12. The method, according to claim 11, wherein said fruit are apples.

13. The method, according to claim 1, wherein said fatty acid is applied between about 10% bloom and about 2 to 3 days after 100% bloom.

14. The method, according to claim 13, wherein said fatty acid is applied between about 60% bloom and about 100% bloom.

15. The method, according to claim 14, wherein said fatty acid is applied within between 2 days before and about 2 days after 100% bloom.

16. The method, according to claim 1, wherein said fatty acid is applied at a concentration of from about 0.25% to about 2% v/v of a 60% formulation, or at an equivalent concentration.

* * * * *

UNITED STATES PATENT AND TRADEMARK OFFICE
CERTIFICATE OF CORRECTION

PATENT NO.   :   5,242,891

DATED        :   September 7, 1993

INVENTOR(S)  :   Thomas E. Larsen, Kenneth D. Abercrombie, R. Hugh Crowley

It is certified that error appears in the above-identified patent and that said Letters Patent is hereby corrected as shown below:

Column 5:   line 59: "optical timing" should read --optimal timing--.

Signed and Sealed this

Fifteenth Day of March, 1994

Attest:

BRUCE LEHMAN

Attesting Officer     Commissioner of Patents and Trademarks